United States Patent
Zhou et al.

(10) Patent No.: US 11,213,297 B2
(45) Date of Patent: Jan. 4, 2022

(54) ATRIAL APPENDAGE OCCLUDER CAPABLE OF ENTERING HALF-RELEASED STATE BY MEANS OF PUSHING HEAD-END FIBER

(71) Applicant: BEIJING MED ZENITH MEDICAL SCIENTIFIC CO., LTD., Beijing (CN)

(72) Inventors: Qingliang Zhou, Beijing (CN); Jinshan Li, Beijing (CN); Jian Meng, Beijing (CN); Danian Ke, Beijing (CN)

(73) Assignee: BEIJING MED ZENITH MEDICAL SCIENTIFIC CO., LTD., Beijing (CN)

( * ) Notice: Subject to any disclaimer, the term of this patent is extended or adjusted under 35 U.S.C. 154(b) by 452 days.

(21) Appl. No.: 16/081,006

(22) PCT Filed: Dec. 20, 2016

(86) PCT No.: PCT/CN2016/110911
§ 371 (c)(1),
(2) Date: Aug. 29, 2018

(87) PCT Pub. No.: WO2017/157071
PCT Pub. Date: Sep. 21, 2017

(65) Prior Publication Data
US 2019/0090885 A1 Mar. 28, 2019

(30) Foreign Application Priority Data
Mar. 14, 2016 (CN) .......................... 201610144567.5

(51) Int. Cl.
*A61B 17/12* (2006.01)
*A61B 17/00* (2006.01)
*A61F 2/02* (2006.01)

(52) U.S. Cl.
CPC .. *A61B 17/12172* (2013.01); *A61B 17/12031* (2013.01); *A61B 17/12122* (2013.01);
(Continued)

(58) Field of Classification Search
CPC ........ A61B 17/12031; A61B 17/12122; A61B 17/12036; A61B 17/12027;
(Continued)

(56) References Cited

U.S. PATENT DOCUMENTS

2014/0257361 A1* 9/2014 Prom ............... A61B 17/12022
606/198
2016/0100844 A1* 4/2016 Li .................... A61B 17/12122
606/200

FOREIGN PATENT DOCUMENTS

CN 104352260 B 11/2017
EP 2074953 A1 7/2009
(Continued)

OTHER PUBLICATIONS

Office Action of the corresponding Russian patent application.
(Continued)

*Primary Examiner* — Majid Jamialahmadi
(74) *Attorney, Agent, or Firm* — Platinum Intellectual Property LLP

(57) ABSTRACT

An atrial appendage occluder capable of entering a half-released state by means of pushing a head-end fiber comprises: an occlude body (1); a head-end control fiber (2); and a tail-end control fiber (3). A head end of the occluder body (1) is connected to one end of the head-end control fiber (2) by means of a head-end threaded bushing (4). A tail end of the occluder body (1) is connected to one end of the tail-end control fiber (3) by means of a tail-end threaded bushing (5). The tail-end control fiber (3) is in the form of a hollow column. The other end of the head-end control fiber (2) sequentially passes through the tail-end threaded bushing (5) and the tail-end control fiber (3). The occluder body (1) is in a woven-net support structure, and has a shape preconfigured to match the structure of an atrial appendage after the occluder body (1) has been fully released. The occluder (Continued)

body (1) is in the form of a strip and disposed in an outer sheath (6) before being released. The occluder body (1) is in a half-release state after being pushed out of the outer sheath (6). The diameter of the occluder body (1) is changed by pushing or pulling the head-end control fiber (2, 3). The atrial appendage occluder can adjust its location in the atrial appendage, such that the occluder can be released precisely in a preset location.

8 Claims, 4 Drawing Sheets

(52) U.S. Cl.
 CPC ...... *A61F 2/02* (2013.01); *A61B 2017/00477* (2013.01); *A61B 2017/00867* (2013.01); *A61B 2017/12095* (2013.01)

(58) Field of Classification Search
 CPC .......... A61B 17/12022; A61B 17/1204; A61B 17/12095; A61B 17/12172; A61B 2017/00477; A61B 2017/12095; A61B 2017/12054

See application file for complete search history.

(56) References Cited

FOREIGN PATENT DOCUMENTS

| RU | 2405473 C2 | 12/2010 |
| RU | 2446773 C2 | 4/2012 |
| WO | 2008040555 A3 | 9/2008 |

OTHER PUBLICATIONS

EPO opinion dated Aug. 6, 2020.
EPO supplementary search report dated Aug. 21, 2019.
Indian Patent Office Examination Report dated Feb. 5, 2021.

\* cited by examiner

ATRIAL APPENDAGE OCCLUDER CAPABLE OF ENTERING HALF-RELEASED STATE BY MEANS OF PUSHING HEAD-END FIBER

TECHNICAL FIELD

The embodiments of the present invention relate to the field of medical equipment, and in particular to an atrial appendage occluder capable of entering a semi-release state by pushing a distal cable.

BACKGROUND OF THE INVENTION

Atrial fibrillation is one of the most common arrhythmias in clinical practice. There are many patients with atrial fibrillation. At present, there are about 8 million patients with atrial fibrillation in China, and the number of patients with atrial fibrillation is increasing year by year. 0.4%4% of the patients with atrial fibrillation may have a stroke every year. That is to say, among the 8 million patients, 32-80 thousand people may have an ischemic stroke due to atrial fibrillation. Stroke is the greatest hazard caused due to atrial fibrillation. It is studied that 15-20% of ischemic strokes are caused by atrial fibrillation, and about one in every six stroke patients has atrial fibrillation. The incidence of stroke in patients with non-valvular atrial fibrillation is 5.6 times that of normal persons, and the incidence of stroke in valvular atrial fibrillation is 17.6 times that of normal persons. Moreover, the consequences of stroke caused by atrial fibrillation are more serious, and the rate of mortality and disability can reach 70%. For patients with valvular atrial fibrillation, 57% of atrial thrombosis originates from left atrial appendages. For patients with non-valvular atrial fibrillation, 90% of left atrial thrombosis originates from left atrial appendages. Even after sinus rhythm is restored, the contraction of the left atrial appendage is stunned so that it is possible to form a thrombus again.

There are three main methods for clinical prevention of atrial fibrillation ischemic stroke. The first method is to take anticoagulant drugs, such as warfarin. However a patient after being applied with warfarin may have a certain risk of bleeding, and must be frequently monitored, and there are lots of contraindications, and clinical application is difficult. In addition, warfarin also has a possibility of causing osteoporosis and soft tissue necrosis. The second method involves directly resection or ligation of the atrial appendage during a cardiac surgical operation, A main defection of the second method is a low rate of complete closure of the left atrial appendage. Previous studies have shown that a success rate of complete resection of the left atrial appendage is up to about 80%, and there is also risk of tearing and bleeding. The third method is to close the left atrial appendage by an instrument and percutaneously intervene the left atrial appendage with a blocking product such as PLAATO, WATCHMAN, ACP, etc. By blocking the left atrial appendage with a left atrial appendage occluder, the incidence of stroke in patients with atrial fibrillation may be reduced. The principle is that the left atrial appendage occluder closes an entrance of the left atrial to left atrial appendage, blocks a blood flow between the left atrial appendage and the left atrium to prevent the thrombus generated in the left atrial appendage from entering the atrium, reducing the risk of stroke. After a period of time, a surface of the occluder is endothelialized, such that the problem of entry of the left atrial appendage thrombus into the left atrium may be thoroughly solved.

At present, an interventional occlusion of the left atrial appendage is a hot spot of research at home and abroad. There are foreign occlusion devices on the market, and domestic occlusion devices are also under development. Because forms of left atrial appendages are different and irregular, there are some difficulties on a matching of an occluder and an atrial appendage. Current atrial appendage occluder has the following disadvantages:

(1) existing atrial appendage occluders are all of a type of one-step release, and are not pre-adjustable. Only when the occluders are completely released, it can be determined whether the occluders are released in place. If the occluders are released at an improper position, the occluders can only be fully withdrawn and released again, and the previous release process will be repeated. Therefore, an accuracy of positioning is poor.

(2) At present, most of the atrial appendage occluders have a barbed structure, if the atrial appendage occulders are released multiple times due to improper released positions, adverse events such as puncture and tear of the atrial appendage may easily occur, causing hurt to patients.

SUMMARY OF THE INVENTION

I. Technical Problem to be Solved

The technical problem to be solved by the embodiments of the present invention is how to adjust a position of an occluder in an atrial appendage, so that the occluder can be accurately released at an intended position, reducing the difficulty of a surgical operation, and improving the success rate of the surgical operation.

II. Technical Solution

In order to solve the above technical problem, an embodiment of the present invention provides an atrial appendage occluder capable of entering a semi-release state by pushing a distal cable. The atrial appendage occluder comprises an occluder body, a distal control cable and a proximal control cable. A distal end of the occluder body is connected to one end of the distal control cable by means of a distal threaded bushing, and a proximal end of the occluder body is connected to one end of the proximal control cable by means of a proximal threaded bushing. The proximal control cable is in a shape of a hollow column, and the other end of the distal control cable is capable of sequentially passing through the proximal threaded bushing and the proximal control cable. The occluder body is in a woven mesh support structure, and has an external shape preconfigured to match a structure of an atrial appendage after being completely released, and the occluder body is in a shape of a strip and disposed in an outer sheath before being released. The occluder body enters a semi-release state after being pushed out of the outer sheath so that a position of the occluder body within the atrial appendage can be adjusted. A diameter of the occluder body is varied by pushing or pulling the distal control cable, to enable the occluder body to be completely released at an intended occlusion position.

In some embodiments, an outer diameter of the distal control cable is smaller than inner diameters of the proximal threaded bushing and the proximal control cable.

In some embodiments, the distal threaded bushing and the proximal threaded bushing are nuts.

In some embodiments, an outer surface of the occluder body is formed as a nickel-titanium wire woven mesh.

In some embodiments, the occluder body is woven by multiple layers of nickel-titanium wire woven mesh.

In some embodiments, the occluder body is woven by a single layer of nickel-titanium wire woven mesh, and a thin film is provided inside the mesh by stitching.

In some embodiments, the thin film is a PET or ePTFE film.

In some embodiments, the distal threaded bushing and the proximal threaded bushing are connected to the occluder body by welding, respectively

III. Advantageous Effects

Compared with the prior art, the embodiments of the invention have the following advantages:

With the atrial appendage occluder capable of entering a semi-release state by pushing a distal cable according to the embodiment of the present invention, a distal end of the occluder body is connected to one end of a distal control cable, and a proximal end of the occluder body is connected to one end of a proximal control cable, and the other end of the distal control cable passes through the other end of the proximal control cable, and the occlude body is arranged to be placed into a semi-release state after being pushed out of an outer sheath so as to make room for adjusting a position of the occluder body in the atrial appendage. A size of the occluder body can be adjusted by pushing or pulling the distal control cable, and the position of the occluder body in the atrial appendage can be adjusted by moving the proximal control cable, so as to ensure that the occluder body can be released at an intended occlusion position in the atrial appendage accurately after being completely released, reducing the difficulty of a surgical operation and improving the success rate of the surgical operation.

An atrial appendage occluder capable of entering a semi-release state by pushing a distal cable according to the embodiments of the present invention is designed according to an anatomical structure of the inner cavity of the left atrial appendage, and can be perfectly matched with the structure of the atrial appendage to achieve an ideal occlusion effect, and at the same time a displacement and detachment of the atrial appendage occluder can be avoided. Further, the atrial appendage occluder can be operated easily, reducing the number of repeated releases and reducing the probability of adverse events.

LIST OF REFERENCE NUMERALS

Figure 1:
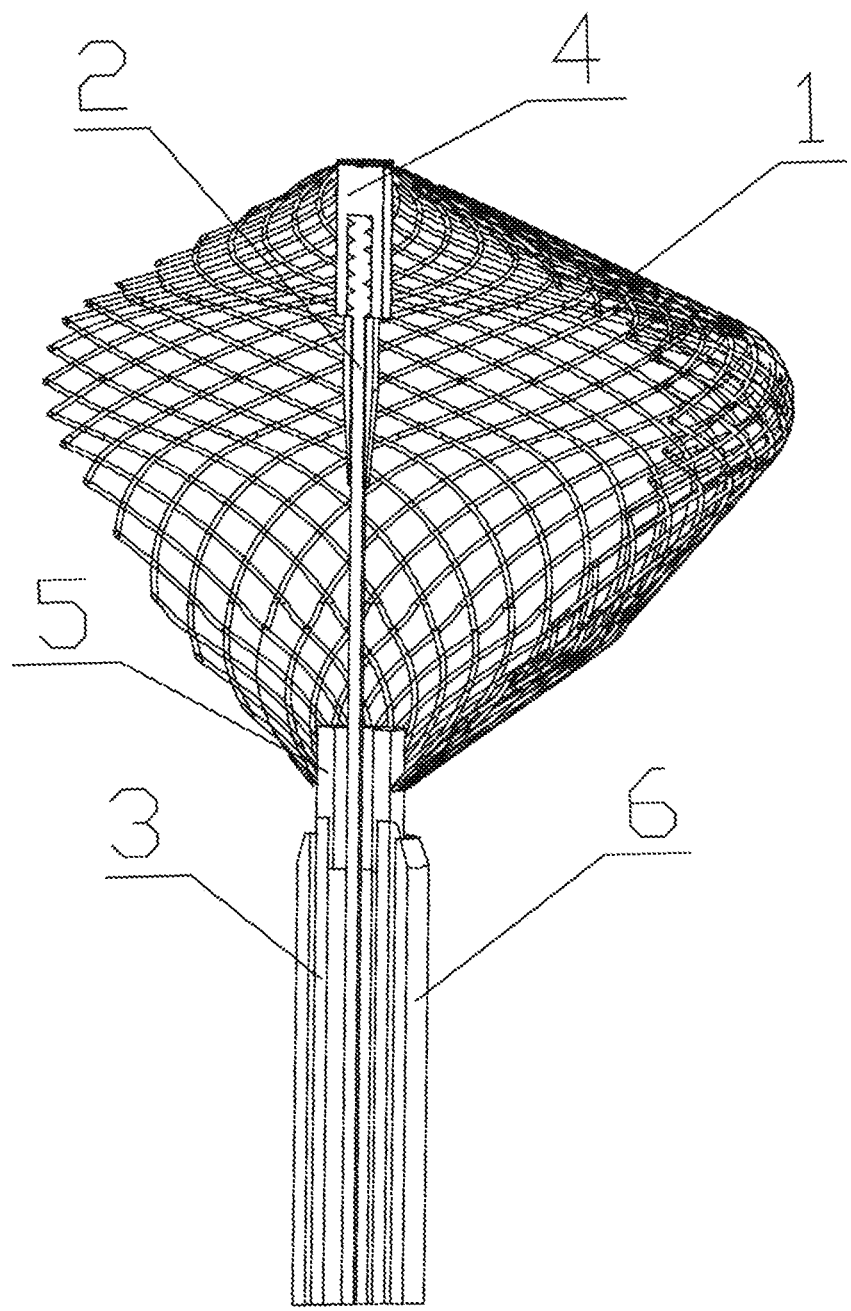
FIG. 1 is an overall longitudinal cross-sectional view of an atrial appendage occluder capable of entering a semi-release state by pushing a distal cable in a semi-release state according to an embodiment of the present invention.

1: occluder body; 2: distal control cable; 3: proximal control cable; 4: distal threaded bushing; 5: proximal threaded bushing; 6: outer sheath; 7: atrial appendage.

DETAILED DESCRIPTION OF THE INVENTION

The specific embodiments of the present invention will be described in detail below in conjunction with the accompanying drawings. The following examples are intended to illustrate the embodiments of the invention, but are not intended to limit the scope of the embodiments of the invention.

In the description of the embodiments of the present invention, it should be noted that the orientation or positional relationship indicated by terms "center", "longitudinal", "lateral", "upper", "lower", "front", "back", "left", "right", "vertical", "horizontal", "top", "bottom", "inside", "outside", etc. are based on the orientation or positional relationship shown in the drawings, and these terms are used simply for the convenience of description of the embodiments of the invention and simplifying the description, rather than indicating or implying that the concerned devices or elements must have a specific orientation or be configured and operated in a specific orientation. Thus, these terms are not to be construed as limiting the embodiments of the invention.

In the description of the embodiments of the present invention, it should be noted that the terms "attach", "couple", and "connect" are to be understood broadly, and may be, for example, a fixed connection or a detachable connection, or an integral connection; may be mechanical connection or electrical connection; may be directly connected, or may be indirectly connected through an intermediate medium, and may be internal communication between the two elements. For a person of ordinary skilled in the art, the specific meanings of the above terms in the embodiments of the present invention can be understood according to specific situations.

Figure 2:
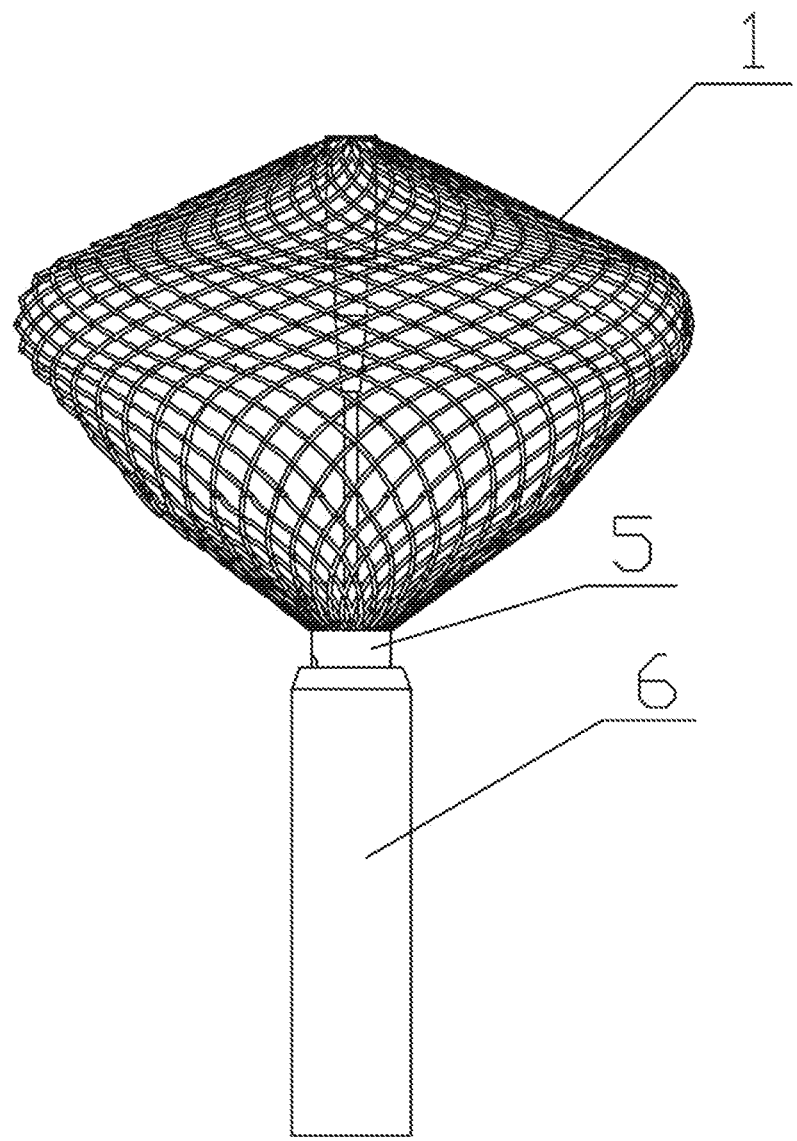
FIG. 2 is an overall schematic structural view of an atrial appendage occluder capable of entering a semi-release state by pushing a distal cable in a semi-release state according to an embodiment of the present invention.
Figure 3:
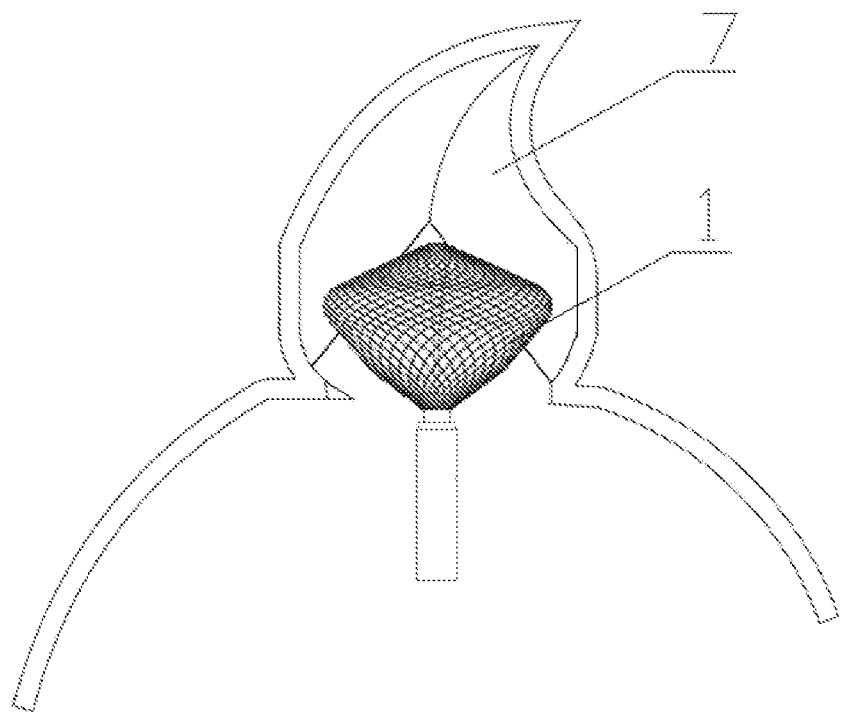
FIG. 3 is a schematic structural view of an atrial appendage occluder capable of entering a semi-release state by pushing a distal cable in a semi-release state within an atrial appendage according to an embodiment of the present invention.

As shown in FIG. 1 and FIG. 2, an atrial appendage occluder capable of entering a semi-release state by pushing a distal cable according to an embodiment of the present invention comprises an occluder body 1, a distal control cable 2 and a proximal control cable 3. A distal end of the occluder body 1 is connected to one end of the distal control cable 2 by means of a distal threaded bushing 4. Specifically, the one end of the distal control cable 2 may be provided with an external thread, and the distal threaded bushing 4 may be provided with an internal thread, and the distal control cable 2 and the distal threaded bushing 4 are screwed together, so that the distal control cable 2 and the distal threaded bushing 4 can be detached by means of unscrewing. A proximal end of the occluder body 1 is connected to one end of the proximal control cable 3 by means of a proximal threaded bushing 5. The proximal control cable 3 is in a shape of a hollow column, and the other end of the distal control cable 2 sequentially passes through the proximal threaded bushing 5 and the proximal control cable 3. The distal end of the occluder body 1 is located above the proximal end of the occluder body 1. The occluder body 1 has a woven mesh support structure, and is pre-configured to have an external shape matching with a structure of the atrial appendage 7 after the occluder body 1 is completely released. Before being released, the occlude body 1 is stretched into a shape of a strip and disposed in the outer sheath 6. In order to minimize a size of the atrial appendage occluder, which can enter a semi-release state by pushing the distal cable, it is preferable that the distal threaded bushing 4 and the proximal threaded bushing 5 have the same outer diameter, to facilitate to be installed into the outer sheath 6. The occluder body 1 will be in the semi-release state after being pushed out of the outer sheath 6, so that a position of the occluder body 1 in the atrial appendage 7 can be adjusted. Since the occluder body 1 is in the semi-release state, it is not completely attached to the atrial appendage 7 (as shown in FIG. 3), so that there is a room for adjustment. By pushing or pulling the distal control fiber 2, a diameter of the occluder body 1 can be varied, that is, the size or dimension of the occluder body 1 can be changed. Further, by moving the proximal control cable 3, the position of the occluder body 1 in the atrial appendage 7 can be adjusted. The two control cables can be operated independently without interfering with each other, so as to completely release the occluder body 1 at an intended occlusion position in the atrial appendage 7 in an accurate way, reducing the difficulty of a surgical operation and improving the success rate of the surgical operation.

Specifically, an outer diameter of the distal control cable 2 is smaller than inner diameters of the proximal threaded bushing 5 and of the proximal control cable 3, so that the distal control cable 2 is capable of moving within the proximal threaded bushing 5 and the proximal control cable 3.

In some embodiments, the distal threaded bushing 4 and the proximal threaded bushing 5 may be nuts, and the distal threaded bushing 4 and the proximal threaded bushing 5 may be welded to the distal end and the proximal end of the occluder body 1 respectively, to form a closed entity.

In some embodiments, an outer surface of the occluder body 1 is a nickel-titanium wire woven mesh, and the nickel-titanium alloy woven mesh is fixed into a predetermined shape by a heat treatment process to form the occluder body 1.

In order to improve the blood-blocking performance, the occluder body 1 is preferably woven by multiple layers of nickel-titanium wire woven mesh to prevent blood exchange between the atrium and the atrial appendage 7.

In addition, the occluder body 1 may also be woven by a single layer of nickel-titanium wire woven mesh. In order to improve a blood-blocking performance, a thin film may be stitched inside the single-layer nickel-titanium wire woven mesh, and the thin film is preferably PET (Polyethylene terephthalate) or ePTFE film (polyporous film formed by expanding and stretching polytetrafluoroethylene).

Figure 4:
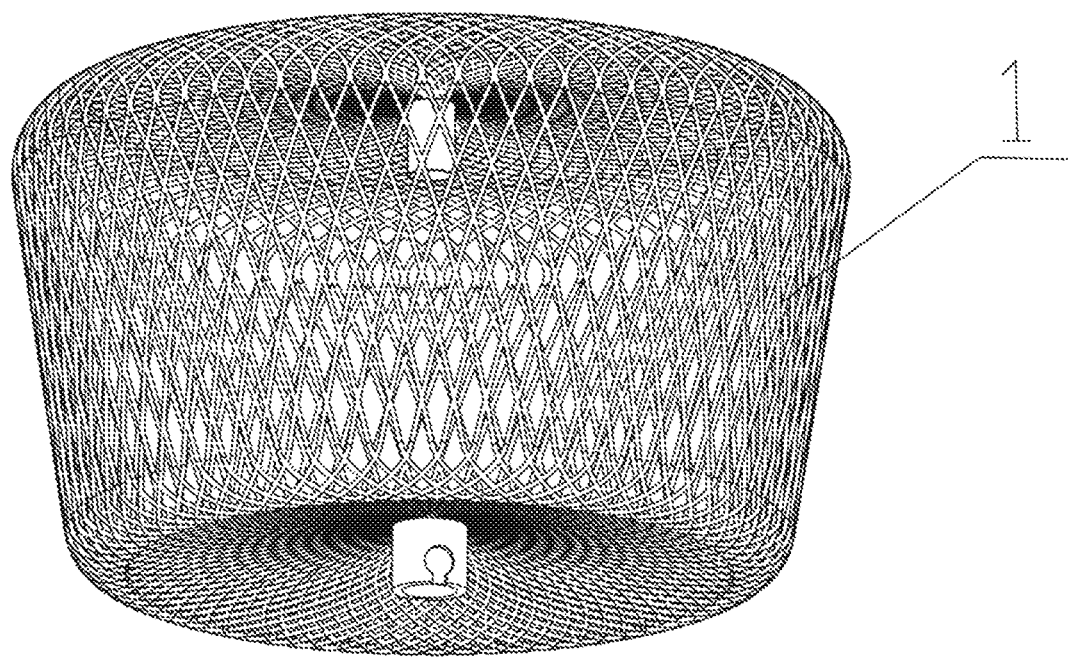
FIG. 4 is a schematic structural view of an atrial appendage occluder capable of entering a semi-release state by pushing a distal cable after being completely released according to an embodiment of the present invention.
Figure 5:
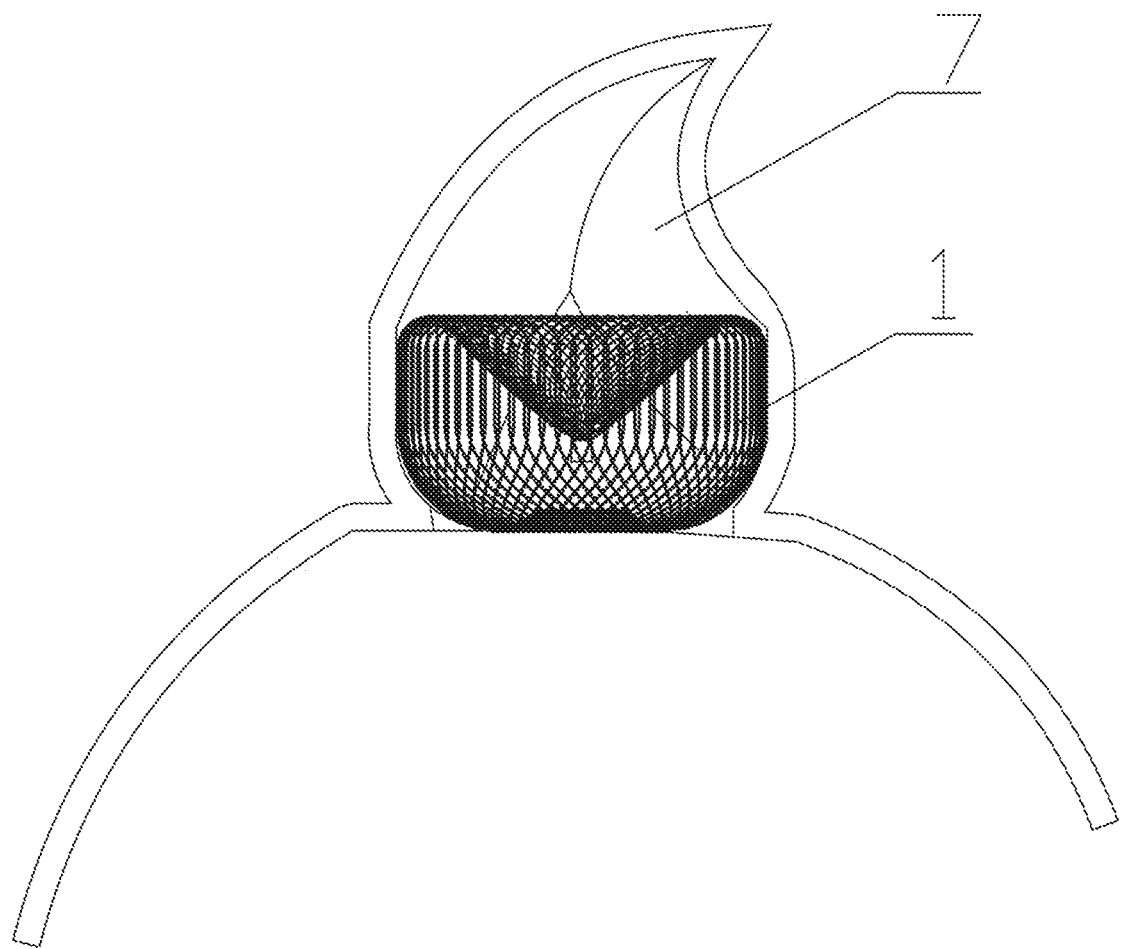
FIG. 5 is a schematic structural view of an atrial appendage occluder capable of entering a semi-release state by pushing a distal cable completely released in the atrial appendage according to an embodiment of the present invention.

Further, as shown in FIG. 4, the occluder body 1 may assume a shape of a cylinder, or a truncated cone with a lager upper portion and smaller lower portion after being completely released, and be placed at an opening of the left atrial appendage 7. By a supporting force of the occluder body 1, the occluder body 1 and an inner wall of the atrial appendage 7 are fully attached to each other snugly (as shown in FIG. 5), and the atrial appendage occluder, which enters a semi-release state by pushing the distal cable, is prevented from being displaced and detached by friction. Of course, after the occluder body 1 is completely released, it can assume other suitable shapes.

It can be seen from the above embodiments that the embodiments of the present invention can adjust a position of the occluder in the atrial appendage 7 so that the occluder can be accurately released at an intended position, thus the difficulty of a surgical operation is reduced, and the success rate of the surgical operation is improved.

An atrial appendage occluder capable of entering a semi-release state by pushing a distal cable according to the embodiments of the present invention is designed according to an anatomical structure of the inner cavity of the left atrial appendage 7, and can be perfectly matched with the structure of the atrial appendage 7 to achieve an ideal occlusion effect, and at the same time a displacement and detachment of the atrial appendage occluder can be avoided. Further, the atrial appendage occluder can be operated easily, reducing the number of repeated releases and reducing the probability of adverse events.

The above is only the preferred embodiments of the present invention, and is not intended to limit the embodiments of the present invention. Any modifications, equivalent substitutions, improvements, etc. within the spirit and principle of the embodiments of the present invention should be included in the scope of protection of the present invention.

What is claimed is:

1. An atrial appendage occluder capable of entering a semi-release state, comprising an occluder body, a distal control cable and a proximal control cable, and wherein,
    a distal end of the occluder body is connected to one end of the distal control cable by means of a distal threaded bushing, wherein a terminal of the distal control cable is ended within the distal threaded bushing and wherein the distal threaded bushing is completely located within the occluder body, and a proximal end of the occluder body is connected to one end of the proximal control cable by means of a proximal threaded bushing being partially located outside of the occluder body; the proximal control cable is in a shape of a hollow column, and the other end of the distal control cable is capable of sequentially passing through the proximal threaded bushing and the proximal control cable; and
    the occluder body is in a woven mesh support structure, and has an external shape preconfigured to match a structure of an atrial appendage after being completely released, and the occluder body is in a shape of a strip and disposed in an outer sheath before being released, and the occluder body is configured to enter the semi-release state after being pushed out of the outer sheath so that a position of the occluder body within the atrial appendage can be adjusted; and a diameter of the occluder body is varied by pushing or pulling the distal control cable, to enable the occluder body to be completely released at an intended occlusion position.

2. The atrial appendage occluder of claim 1, wherein an outer diameter of the distal control cable is smaller than inner diameters of the proximal threaded bushing and the proximal control cable.

3. The atrial appendage occluder of claim 1, wherein the distal threaded bushing and the proximal threaded bushing are nuts.

4. The atrial appendage occluder of claim 1, wherein an outer surface of the occluder body is formed as a nickel-titanium wire woven mesh.

5. The atrial appendage occluder of claim 1, wherein the occluder body is woven by multiple layers of nickel-titanium wire woven mesh.

6. The atrial appendage occluder of claim 1, wherein the occluder body is woven by a single layer of nickel-titanium wire woven mesh, and a thin film is provided inside the mesh by stitching.

7. The atrial appendage occluder of claim 6, wherein the thin film is a PET or ePTFE film.

8. The atrial appendage occluder of claim 1, wherein the distal threaded bushing and the proximal threaded bushing are connected to the occluder body by welding, respectively.

* * * * *